United States Patent
Schaefer, Jr. et al.

(10) Patent No.: US 11,243,182 B2
(45) Date of Patent: Feb. 8, 2022

(54) MOISTURE SOIL PROBE SYSTEM

(71) Applicant: AGI Suretrack LLC, Osceola, MO (US)

(72) Inventors: Donald B. Schaefer, Jr., Lake Winnebago, MO (US); Glenn Dowe Wiskur, Butler, MO (US); Tianyu Lin, Raymore, MO (US); Trevor Hodgson, Archie, MO (US)

(73) Assignee: AGI SURETRACK LLC, Osceola, MO (US)

(*) Notice: Subject to any disclaimer, the term of this patent is extended or adjusted under 35 U.S.C. 154(b) by 123 days.

(21) Appl. No.: 16/781,455

(22) Filed: Feb. 4, 2020

(65) Prior Publication Data

US 2020/0249191 A1 Aug. 6, 2020

Related U.S. Application Data

(60) Provisional application No. 62/801,443, filed on Feb. 5, 2019.

(51) Int. Cl.
*G01N 27/22* (2006.01)
*G01N 33/24* (2006.01)

(52) U.S. Cl.
CPC ......... *G01N 27/223* (2013.01); *G01N 33/246* (2013.01)

(58) Field of Classification Search
CPC .................. G01N 27/223; G01N 33/246
USPC ................ 324/667, 664, 663, 658, 649, 600
See application file for complete search history.

(56) References Cited

U.S. PATENT DOCUMENTS

| | | | | |
|---|---|---|---|---|
| 3,979,667 A | * | 9/1976 | Cornes | G01R 17/16 324/694 |
| 4,020,417 A | * | 4/1977 | Brehob | G01N 27/048 324/694 |
| 5,663,649 A | * | 9/1997 | Topp | E02D 1/027 324/643 |
| 7,535,237 B1 | * | 5/2009 | Campbell | G01N 27/223 324/644 |
| 7,810,515 B2 | * | 10/2010 | Nies | A01G 25/167 137/78.3 |
| 2008/0303138 A1 | * | 12/2008 | Flett | H01L 25/18 257/714 |

* cited by examiner

*Primary Examiner* — Giovanni Astacio-Oquendo
(74) *Attorney, Agent, or Firm* — Tarolli, Sundheim, Covell & Tummino LLP

(57) ABSTRACT

A moisture soil probe system includes a probe having a solid rod with a plurality of sensors attached around the outer circumference of the rod in close proximity to the soil being measured, covered by a waterproof coating. A wireless transmitter unit receives a precision GPS timing signal which is propagated to logic and control circuitry associated with each sensor for use in calculating a volumetric moisture content of the soil in proximity to the sensor. The calculated moisture content is transmitted back to the wireless control unit which further transmits the data to a central station.

18 Claims, 7 Drawing Sheets

MOISTURE SOIL PROBE SYSTEM

CROSS-REFERENCE TO RELATED APPLICATIONS

This application claims the benefit of U.S. provisional patent application Ser. No. 62/801,443, filed Feb. 5, 2019, the contents of which are incorporated herein by reference.

BACKGROUND

Various types of moisture soil probes are used in the field of agriculture to measure the amount of moisture in the soil. While having some similarities, the various probes typically vary in the type and number of sensors used to detect and measure the moisture content of the soil, and in the type of measurement provided. One common type of probe uses one or more sensors to measure the capacitance of the soil surrounding the sensor, with the measured capacitance converted—either at the probe or offboard—to a corresponding volumetric water content. Such probes typically include multiple sensors positioned at intervals along the probe to provide multiple measurements corresponding to the moisture content at various depths in the soil. Many probes further include a temperature sensor positioned alongside the capacitance sensor to provide corresponding soil temperature measurements.

Current technology for capacitive-based soil moisture probes commonly uses strips of conductive metal foil (typically copper) wrapped in a circular pattern to form adjacent rings which act as the plates of a capacitor formed by the rings. Thus formed, and with an electrical signal applied, an electrical fringe field exists between the pair of adjacent rings, with the fringe field being a function of the capacitance of the combination of: (1) the geometry of the rings/plates, (2) the dielectric between the plates and the shell or covering of the probe, (3) the dielectric of the internal material of the probe, and (4) the dielectric of the probe surroundings, which is the soil in which the probe is inserted.

In the case of a soil moisture probe, the first three of those contributors to the combined capacitance are essentially fixed or constant, with the dielectric of the soil being the only variable. Because wet soil has a much higher dielectric constant than dry soil, a change in soil moisture results in a change in the soil dielectric and thus a change in combined capacitance. When the combined "capacitor" is used as part of an oscillator circuit, a change in soil moisture will result in a change in the frequency of the oscillator circuit and thus the soil moisture can be ascertained from the oscillator frequency.

The accuracy of such soil moisture measurements is dependent on several factors, including the accuracy of the time base used in determining the frequency of the oscillator. The frequency of the oscillator is typically determined by counting the number of oscillation cycles during a precise time period, with an independent time base used as the source for the precise time period. Known soil probes commonly use a crystal or a tuning-fork based oscillator to establish the precise time period. However, crystals and tuning-fork devices are highly susceptible to failure due to mechanical shock, thus soil moisture probes employing such devices must generally be handled with care to avoid damage, which greatly limits the methods that can be used to install and remove the probes.

In addition to the accuracy of the time base, the correlation of the frequency of the oscillator circuit to the volumetric moisture in the soil contributes to the overall accuracy of the moisture soil probe. Because the soil acts a dielectric to the aggregate capacitor of the probe as described above, ideally the soil would only affect the capacitive element of the capacitor. However, because a capacitor also comprises a resistive element, attributes of the soil can affect that resistive element and alter the frequency of the oscillator. For example, the conductivity of soil varies based on the presence of salt, moisture, and other elements in the soil. Those elements in the soil thus affect the resistive component of the soil acting as a dielectric, and thus affect the frequency of the oscillator circuit. For example, soils with a higher salt content will result in a different frequency of the oscillator than the same soil would at the same moisture content but having less salt. Moisture soil probes of the prior art typically operate at a nominal frequency of about 100 MHz, which allows errors and variance to be introduced into the measurement of volumetric moisture content in the soil due to salt or other elements present in the soil that affect the resistive component.

Known moisture soil probes are typically formed using a hollow cylindrical tube which contains the sensor and oscillator electronic circuitry. The circuitry is inserted into the tube, with an epoxy or other potting material used to fill the tube and encase the circuitry. Because of the relatively large diameter of the tube—typically one inch or greater—installation of the soil probe requires drilling or digging a hole to receive the probe, then backfilling soil around the probe. And, because of the fragility of the wall of the hollow tube and the potential of impact damage to the crystal or tuning-fork used in the oscillator circuitry, the probes cannot be hammered or pounded into the ground. Removal of the probes from the soil is similarly complex, requiring digging the probe from the ground with the potential of damaging or bending the thin outer wall.

Furthermore, because the wall of the hollow tube provides structural support and rigidity to the tube, it requires that the enclosed circuitry, including the foil plates of the capacitive sensors, be positioned at a relatively far distance from the soil into which the probe is placed. Because the electrical fringe field between the plates decreases exponentially in relation to the distance from the plates, the further the plates are from the soil, the less sensitive the field is to soil moisture.

Thus, it can be seen that there remains a need in the art for a moisture soil probe that is easy to install and remove, is durable, and that has improved accuracy over devices known in the art.

SUMMARY

Embodiments of the invention are defined by the claims below, not this summary. A high-level overview of various aspects of the invention is provided here to introduce a selection of concepts that are further described in the detailed description section below. This summary is not intended to identify key features or essential features of the claimed subject matter, nor is it intended to be used in isolation to determine the scope of the claimed subject matter. In brief, this disclosure describes, among other things, a moisture soil probe system for measuring the volumetric moisture content of soil.

In one embodiment, the moisture soil probe system includes a probe, a wireless transmitter unit, and a battery pack that provides power to circuitry within the wireless control unit and to sensors on the probe.

The probe comprises a solid rod, with a plurality of sensors attached to the outer surface of the rod along its length of the rod to allow measurement of moisture content at various depths when the probe is installed in soil. A waterproof covering encapsulates the plurality of sensors and protects them from moisture. A cap having interior threads is attached at an upper end of the probe, with a pointed tip at the lower end. In one aspect, the solid rod allows the probe to be driven into the ground by hammering. In another aspect, the threaded cap allows the attachment of a slide hammer to install and remove the probe without damage or digging. In a further aspect, the positioning of the sensors and sensor circuitry on the outer periphery of the rod allows the circuitry to be in close proximity to the soil being measured, allowing more precise and accurate measurement of moisture content.

The wireless transmitter unit includes GPS circuitry operable to receive a GPS timing signal and to propagate a precise timing signal to logic and control circuitry of each of the sensors. In one aspect, the use of the GPS timing signal provides an accurate precision time base allowing more accurate and precise measurement of moisture content of the soil.

In a further aspect, the battery pack is configured to be buried in the ground or soil, with wireless transmitter unit positioned atop or in proximity to the battery pack, with the upper end of the probe exposed and positioned flush with the soil.

DESCRIPTION OF THE DRAWINGS

Illustrative embodiments of the invention are described in detail below with reference to the attached drawing figures, and wherein.

DETAILED DESCRIPTION

The subject matter of select embodiments of the invention is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described. The terms "about" or "approximately" as used herein denote deviations from the exact value in the form of changes or deviations that are insignificant to the function.

Embodiments of the invention include apparatus, systems, and methods for measuring volumetric soil moisture using a probe device and auxiliary circuitry.

Figure 1:
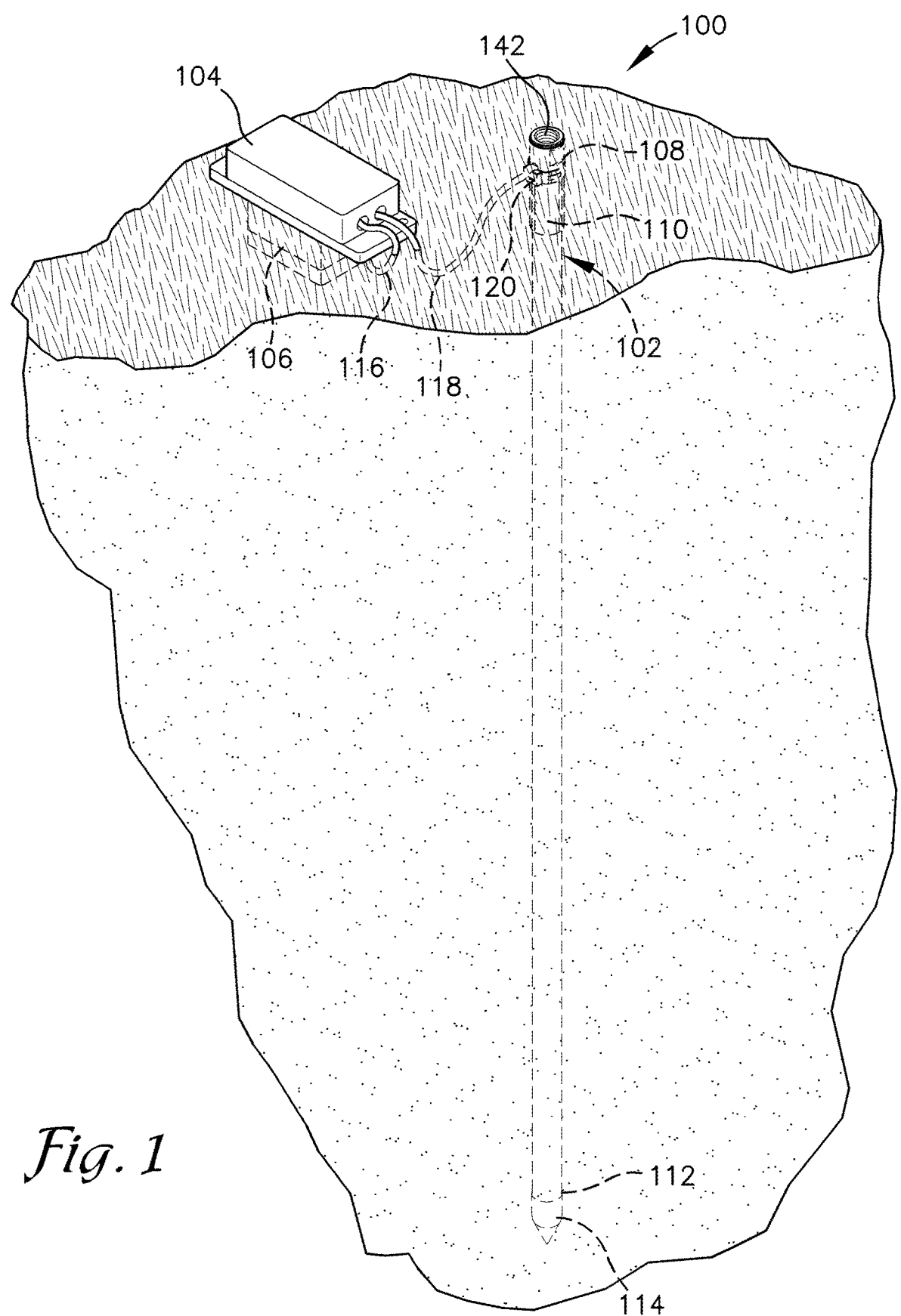
FIG. 1 is a perspective environmental view of a moisture soil probe, wireless transmitter unit, and battery pack installed into the ground in accordance with an exemplary embodiment of the present invention.

Looking first to FIG. 1, a moisture soil probe system 100 generally comprises a moisture soil probe 102 in electrical communication with a wireless transmitter unit 104, with a battery pack 106 supplying power to circuitry contained within the wireless transmitter unit 104 and within the moisture soil probe 102.

As seen in FIG. 1, the moisture soil probe 102 is an elongated cylindrical rod extending between an upper end 108 having a cap 110 with a generally flat upper surface and a lower end 112 having a pointed tip 114. With the system 100 in use as depicted in the figure, the moisture soil probe 102 is embedded into the ground in which the moisture content is to be measured in a substantially vertical orientation, with the upper surface of the cap 110 generally flush with the upper surface of the soil, and the tip 114 embedded deep in the soil at the lower end 112 of the probe 102. The pointed tip 114 punctures the upper surface of the soil and facilitates incursion of the body of the probe 102 into and through the underlying soil.

In one embodiment, as depicted in FIG. 1, the battery pack 106 is attached to the bottom surface of the wireless transmitter unit 104, preferably via a magnetic connection between the two housings, with a magnet attached to the battery pack 106 and a metal surface attached to the wireless transmitter unit 104, or vice versa. In alternative embodiments, the battery pack 106 may unattached and positioned adjacent to or in proximity to the wireless transmitter unit 104.

A first cable 116 comprising a plurality of wires provides electrical communication between the battery pack 106 and the wireless transmitter unit 104 to allow the battery pack to power circuitry within the wireless transmitter unit. A second cable 118 comprising a plurality of wires provides electrical communication between the wireless transmitter unit 104 and the moisture soil probe 102 to further provide power from the battery pack to circuitry within the probe and to also allow data to be transmitted and received between the probe and the wireless transmitter unit. In alternative embodiments, battery pack 106 may be buried deeper into the soil and not attached to the wireless transmitter unit 104 which sits atop the soil surface.

As seen in the figure, in use the wireless transmitter unit 104 rests on top of the soil with attached battery pack 106 buried in the soil adjacent the moisture soil probe 102 with the lower surface of the wireless transmitter unit 104 positioned substantially flush with the upper surface of the soil, and with the first and second cables 116, 118 buried in the soil. A strain relief clamp 120 positioned and attached at the upper end 108 of the probe secures the second cable 118 at its entry to the probe to prevent stress to the cable and/or pulling the cable from the probe.

Battery pack 106 comprises a rectangular shaped enclosure, comprising multiple panels, preferably containing two D-cell type batteries. In alternative embodiments, other battery sizes or power sources may be used. Preferably the case allows opening, such as by removing a side panel, to access and replace the batteries as necessary. A connector positioned on one of the panels is in electrical communication with the batteries and is configured to mate with first cable 116 to provide power to the wireless transmitter unit 104. The connector may be a coaxial connector, plug in connector, or other type of connector known in the art. Preferably one or more magnets are positioned on the upper panel of the battery pack 106 to allow the pack to be attached to mating metal strips on the lower panel of the wireless transmitter unit 104. Thus, the battery pack 106 can be quickly and easily attached to and removed from the wireless transmitter unit 104. The magnetic attachment keeps the battery pack 106 in proximity to the wireless transmitter unit 104 when the two are positioned as depicted in FIG. 1. In alternative embodiments, the battery back 106 may be buried deeper in the ground, or positioned away from the wireless transmitter unit, in which case the two are not magnetically coupled or otherwise attached together.

Wireless transmitter unit 104 comprises GPS circuitry operable to receive signals from the network of global positioning system satellites as is known in the art. Using the timing signal from the GPS signal, circuitry within the wireless transmitter unit 104 provides a precision timing signal. As will be explained in more detail below, the measurement circuitry in the moisture soil probe uses the precision timing signal provided by the wireless transmitter unit in its calculations of volumetric moisture by counting pulses of the oscillator circuit over a precision time period. The antenna portion of the GPS circuitry is preferably positioned against the upper panel of the of enclosure of the wireless transmitter unit 104 such that the antenna has an essentially unobstructed view of the sky to receive signals from the GPS satellites.

Figure 2:
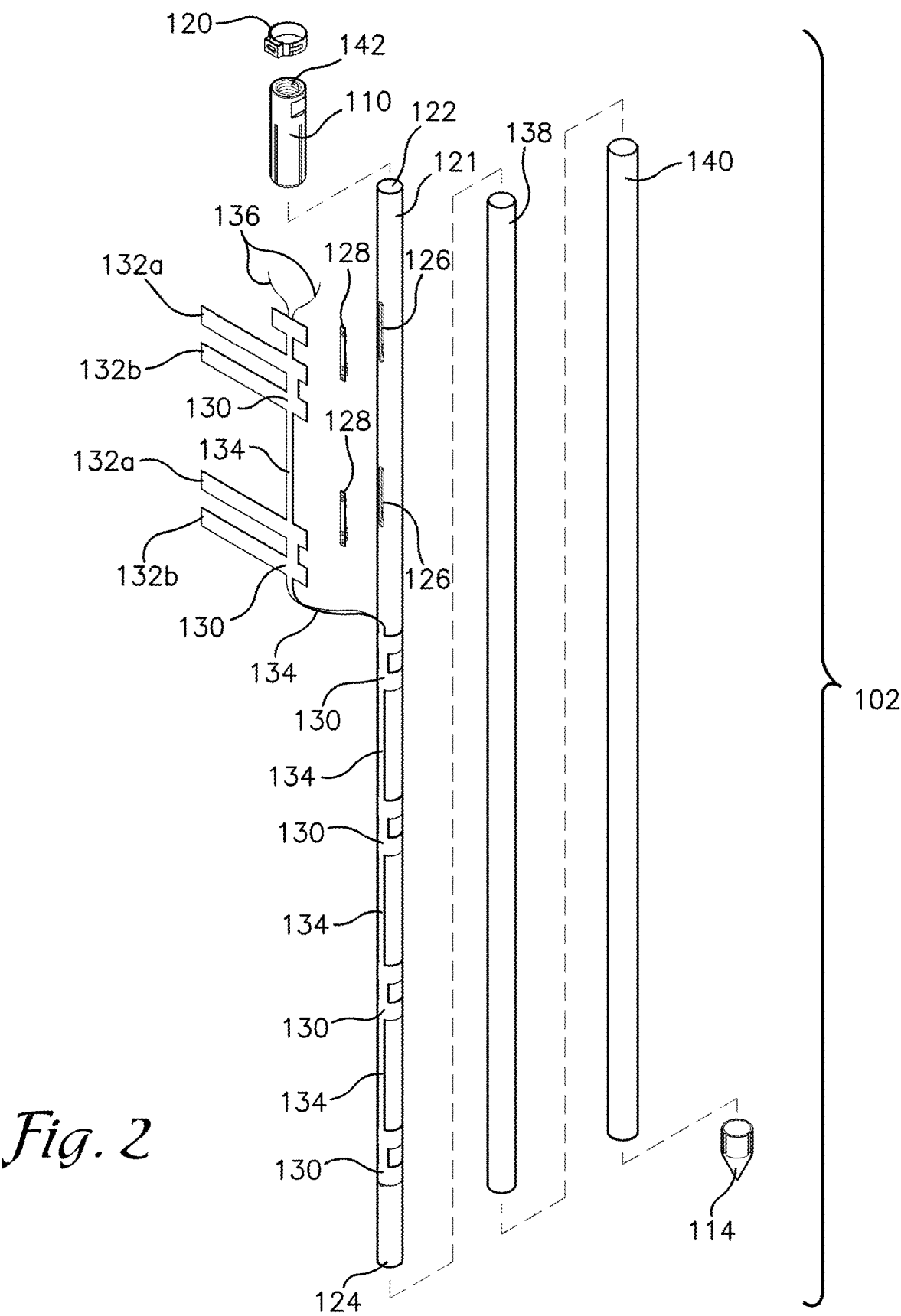
FIG. 2 is an exploded view of the moisture soil probe of FIG. 1.
Figure 7:
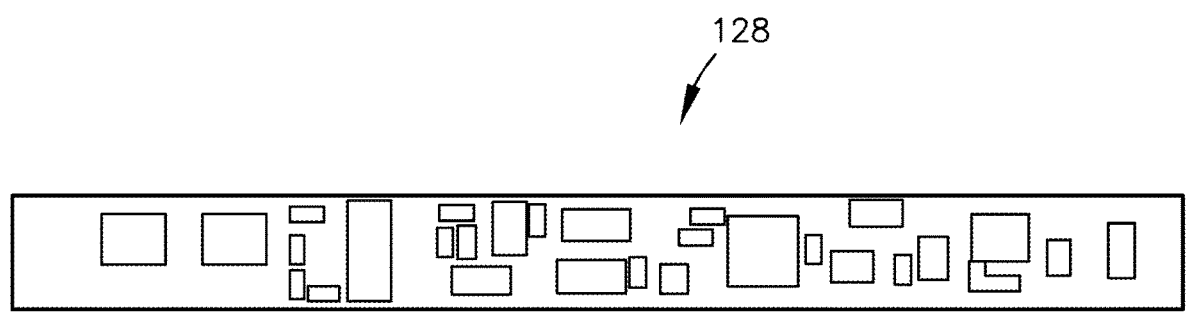
FIG. 7 is a close-up top view of the logic and control circuit board for the sensors of the moisture soil probe of FIG. 1

Looking to FIG. 2, an exploded view of the moisture soil probe 102 is depicted. The probe 102 comprises an elongated solid cylindrical rod 121 extending between a first end 122 and a second end 124. A series of six recessed rectangular slots 126 are formed at intervals along the length of the rod 121, configured to receive a similarly shaped logic circuit board 128 containing logic and control circuitry (as depicted in FIG. 7) for measuring the volumetric moisture content of soil surrounding the probe 102 in the area of the measuring circuitry. Preferably, rod 121 is made of a rigid, water resistant material, such as fiberglass or other fiber reinforced thermoset resin, having a diameter of approximately one-half inch. In alternative embodiments, the rod 121 may be made of other strong, rigid materials, such as composites or plastics.

A series of interconnected flexible circuit boards 130, each adjacent a corresponding slot and corresponding circuit board, are positioned along the length of the rod 121. Each flexible circuit board 130 includes two rectangular tabs 132a, 132b which form the plates of a capacitor used to detect moisture in the soil as previously discussed.

As shown in FIG. 2, six separate moisture sensors are formed along the length of the rod 121, each comprised of a logic circuit board 128 having logic and control circuitry, with a flexible circuit board 130 attached to and in electrical communication with the logic circuit board, such as by soldering or other electrical connection. With the logic circuit board 128 positioned in the slot, the two tabs 132a, 132b of each flexible circuit board 130 are wrapped around the circumference of the rod 121 to contain the logic circuit board 128 thereunder, with the wrapped tabs 132a, 132b forming the plates of a capacitor used by the logic and control circuitry to measure the volumetric moisture content of the soil in proximity to the plates of the capacitor.

Interconnecting flexible circuit boards 134 extend between adjacent flexible circuit boards 130 to provide power and data communications paths to each of the logic circuit boards 128. At the uppermost flexible circuit board 130, a pair of wires 136 extends upwardly and outwardly, and connect to the second cable 118 (as shown in FIG. 1) so that the wireless transmitter module 104 is in communication with each of the logic circuit boards 128.

A first shrink wrap coating 138 substantially covers the rod 121, encapsulating the slots 126, logic circuit boards, flexible circuit boards 130, and interconnecting flexible circuit boards 134, with only the pair of wire 136 extending from under the coating. A second shrink wrap coating 140 covers the first shrink wrap coating 138 to provide additional protection to provide additional abrasion and tear resistance. Preferably the first shrink wrap coating 138 is an adhesive type shrink wrap, with an inner coating of adhesive that is melted on installation to create a semi-rigid and waterproof barrier covering the rod 121 and attached circuitry.

Cap 110 and pointed tip 114 are attached to the upper and lower ends of the rod 121, respectively, with strain relief clamp 120 attached around the outer circumference of cap 110 to attach and secure second cable 118 as depicted in FIG. 1 and described previously.

Figures 5, 6:
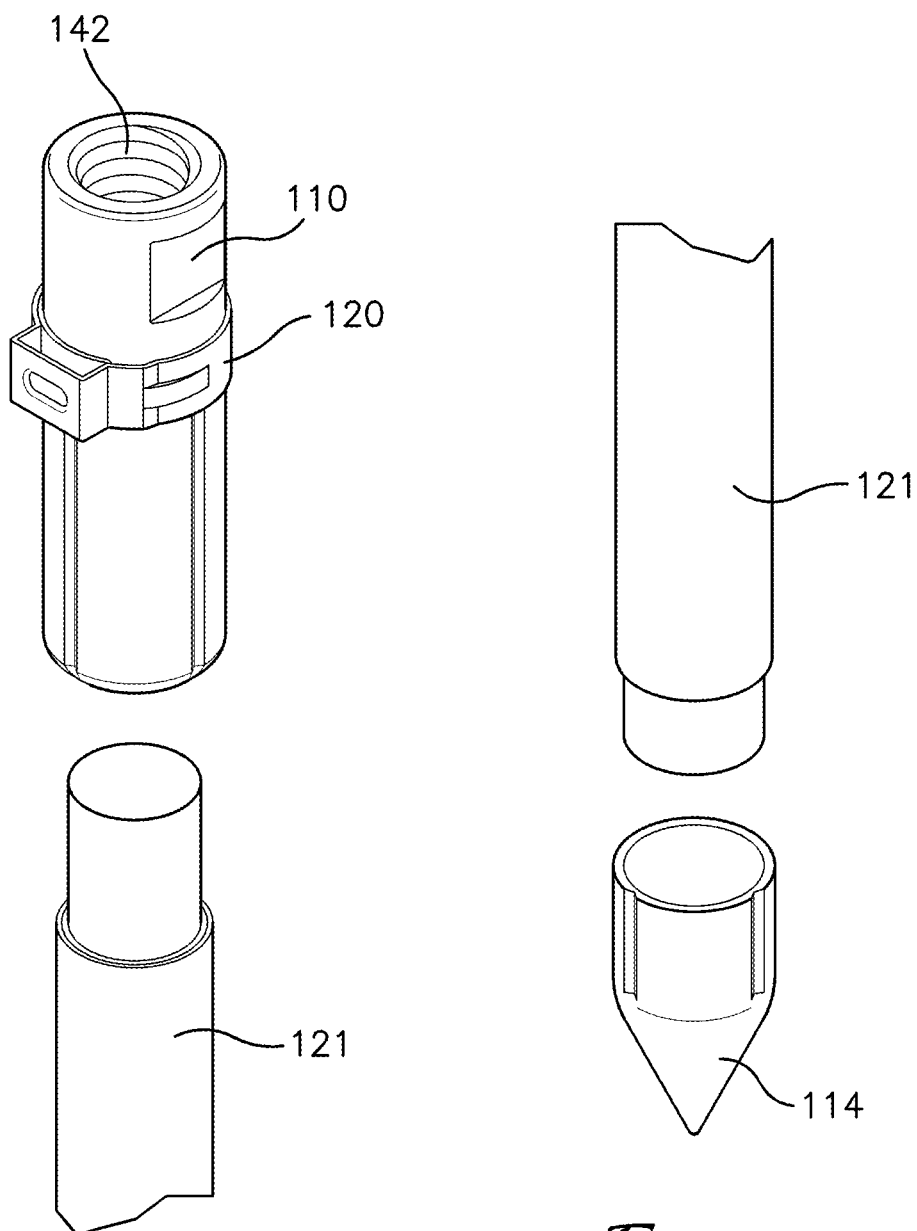
FIG. 5 is a close-up exploded view of the upper end portion of the moisture soil probe of FIG. 1.
FIG. 6 is a close-up exploded view of the lower end portion of the moisture soil probe of FIG. 1.

Turning to FIGS. 5 and 6 cap 110 and pointed tip 114 are preferably attached to the respective ends of rod 121 by crimping, with the crimp process deflecting and embedding a portion of the cap and tip into the fiberglass rod to form a permanent connection. As also seen in FIGS. 5 and 6, cap 110 and pointed tip 114 are preferably attached over a smaller diameter portion at each end of the rod 121. Most preferably, the outer diameters of the cap 110 and pointed tip 114 are approximately the same as the nominal outer diameter of rod 121 with the first and second shrink wrap coatings 138, 140 in place after the cap 110 and pointed tip 114 have been attached.

Figure 3:
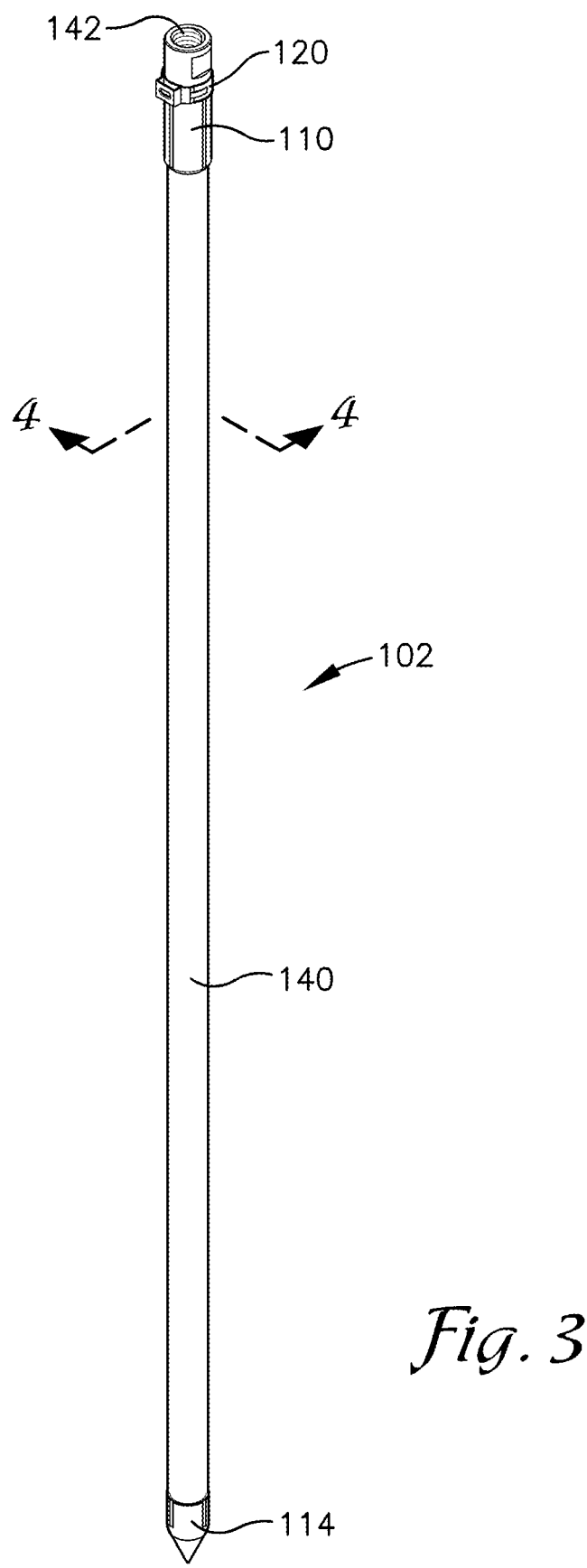
FIG. 3 is an assembled view of the moisture soil probe of FIG. 1.

As seen in FIG. 3, with the components of the moisture soil probe 120 assembled, the outer surface of the second shrink wrap coating 140 covers nearly the entirety of the rod, with the circuit boards and circuitry completely encased and lying just underneath the outer coating.

Figure 4:
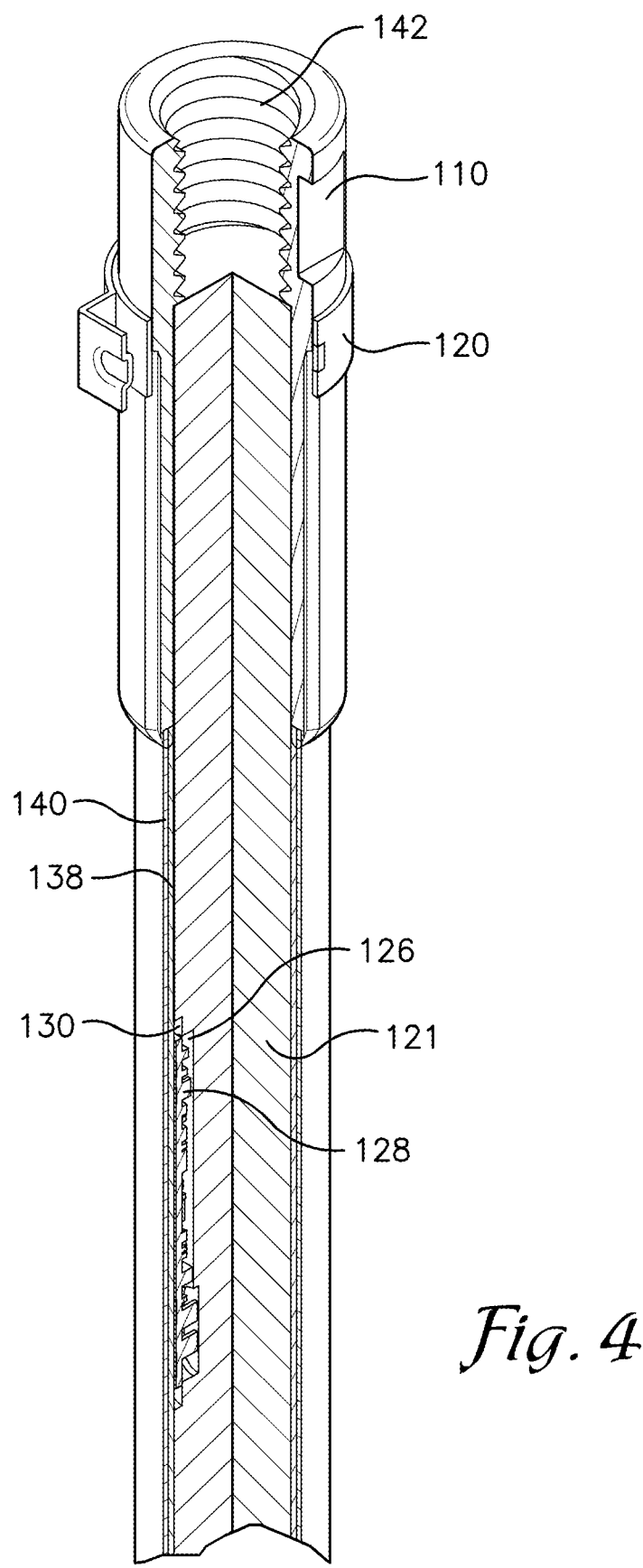
FIG. 4 is a close-up cross-sectional view of the upper portion of the moisture soil probe of FIG. 1.

Looking to the cross-sectional view of FIG. 4, the flexible circuit board 130 and the corresponding tabs forming the plates of the capacitor lie atop the logic circuitry board 128 contained in the slot 126, with only the thicknesses of the first and second shrink wrap coatings 138, 140 separating the plates from the soil surrounding the probe. Thus, when inserted into the soil the plates are in close proximity to the soil being measured.

Figure 8:
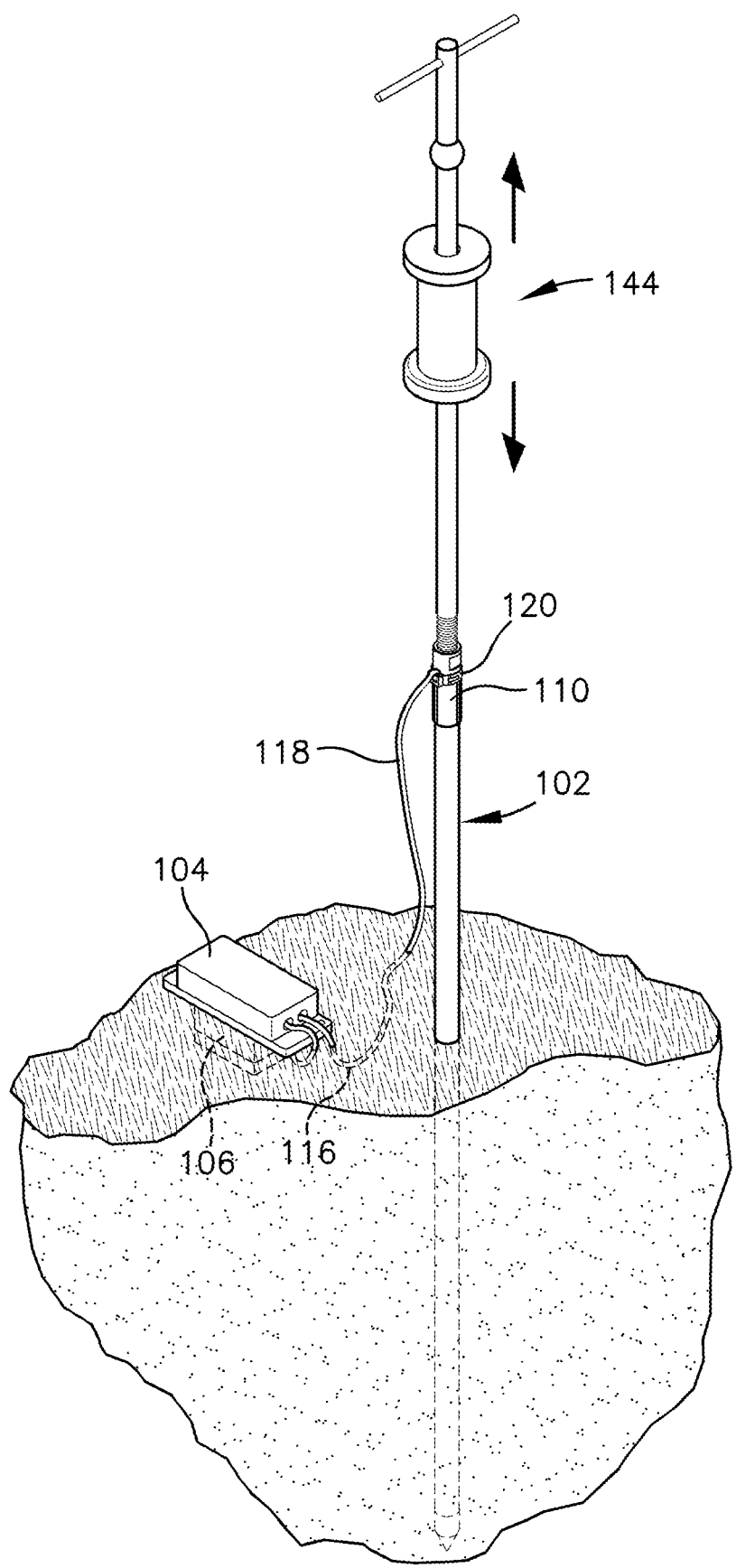
FIG. 8 is a perspective environmental view of the moisture soil probe of FIG. 1 being removed from the ground using a slide hammer attachment.

Looking still to FIGS. 4 and 5, cap 110 comprises interior threading 142 at its upper end. As seen in FIG. 8, the threading allows attachment of a slide hammer device 144 that can be used to install the probe (by pounding the probe into the ground) and to remove the probe (by pulling the probe from the ground). Preferably, when installed, a threaded bolt is mated to the interior threading 142 to protect against debris entering the thread cavity. In alternative installations, a threaded bolt may be engaged with the interior threading 142 allowing the probe to be installed by striking the top of the probe with a hammer to drive it into the ground. Because of the relatively small diameter of the probe and solid interior rod, installation using a slide hammer or mallet will not damage the probe. Likewise, because the timing signal used by the logic and control circuitry is derived from the wireless transmitter 104 (as will be discussed in more detail below) the probe does not use a crystal or tuning fork and thus is not susceptible to damage in that respect by hammering or impact.

With the structure of the moisture soil probe set forth, the use and operation of the moisture soil probe system will now be described.

In use, the probe 102 is driven into the soil at a desired location using a slide hammer (as depicted in FIG. 8) or other appropriate method. With the probe 102 installed into the soil and connected to the wireless transmitter unit 106 and battery pack 104 via first and second cables 116, 118, respectively, the installed system resembles that depicted in FIG. 1.

As described above, the probe 102 comprises six separate moisture sensors, each comprising a logic circuit board 128 and flexible circuit board 130 which forms a capacitor sensitive to moisture in the adjacent soil, with the soil acting as a dielectric between the plates (tabs) of the capacitor. Because the soil acts as the dielectric of the formed capacitor, the moisture content of the soil affects the properties of the dielectric (i.e., the soil). Thus, changes in moisture content change the effective capacitance of the formed capacitor. Using the formed capacitor in the oscillator circuitry, the frequency of oscillation thus varies depending on the moisture content of the soil, and the volumetric moisture content of the soil is determined as follows.

Each logic circuit board 128 comprises oscillator circuitry and logic and control circuitry operable to: count pulses of the oscillator circuitry over a specified period of time; determine the frequency of the oscillator from the counted pulses; calculate a volumetric moisture content based on the determined frequency; and transmit the calculated volumetric moisture content to the wireless transmitter unit 104. With the six sensors positioned along the length of the probe 102, six separate volumetric moisture content measurements are provided, each corresponding to the moisture content in the soil at the depth surrounding the corresponding sensor.

Preferably, the oscillator circuitry on each logic circuit board 128 operates at a nominal frequency of at least 200 MHz so that the capacitive element of each sensor dominates the resistive element to minimize the effect of salt or other materials in the soil on the moisture measurement.

While the logic and control circuitry on each logic circuit board 128 includes timing circuitry, at regular intervals the wireless control unit provides a precise timing signal to each logic circuit board so that each has a precision time signal for use in counting the number of pulses (i.e., frequency) over a precise time interval. Calculated volumetric moisture content is transmitted from each logic circuit board 128 upon command from the wireless transmitter unit 104.

Battery pack 106 provides power to the GPS circuitry within the wireless transmitter unit 104, with logic and control circuitry within the wireless transmitter unit operable to receive a timing signal from the GPS signal. Wireless transmitter unit 104 further includes communication circuitry allowing the unit to transmit and receive to and from a remote device. Thus, the periodic volumetric moisture content readings received from the six sensors on the probe are stored on the wireless transmitter unit and are also available for transmission to a remote station, computer, or server for storage, aggregation, and analysis. Furthermore, a plurality of moisture soil probe systems may be deployed, with all of them reporting to a single central station.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. A moisture soil probe system for measuring moisture content in soil, a probe comprising:
   an elongated solid rod with a plurality of sensors attached along an outer surface of the rod, wherein each of the plurality of sensors is configured to determine a moisture content of soil in proximity to each of the plurality of sensors; and
   a wireless transmitter in communication with the plurality of sensors, the wireless transmitter operable to receive a GPS timing signal and to propagate a precise timing signal to each of the plurality of sensors.

2. The system of claim 1, wherein at least one of the plurality of sensors comprises flex circuitry attached to micro circuit boards housing logic and control circuitry.

3. The system of claim 2, wherein the flex circuitry comprises adjacent tabs, and wherein the adjacent tabs form the plates of a capacitive element of the logic and control circuitry.

4. The system of claim 1, further comprising a coating covering substantially the entirety of the probe and encasing the plurality of sensors.

5. The system of claim 1, wherein the probe comprises a cap attached to an upper end, the cap comprising internal threading allowing attachment of a slide hammer for installation and removal of the probe.

6. The system of claim 1, further comprising a battery pack in electrical communication with the wireless transmitter and/or the plurality of sensors.

7. The system of claim 6, wherein the battery pack and wireless transmitter are magnetically coupled.

8. The system of claim 1, wherein each of the plurality of sensors comprises oscillator circuitry and logic and control circuitry, and wherein the logic and control circuitry comprises a microprocessor programmed to:
   count pulses generated by the oscillator circuitry over a predetermined period of time and determine the frequency of the oscillator therefrom;
   calculate a volumetric moisture content based on the determined frequency; and
   transmit the calculated volumetric moisture content to the wireless transmitter unit for access by a remote device.

9. The system of claim 8, wherein the oscillator operates at a nominal frequency of approximately 200 MHz or greater.

10. A method for measuring moisture content in soil, comprising:
    providing a probe comprising an elongated solid rod with a plurality of sensors attached along an outer surface of the rod, wherein each of the plurality of sensors is configured to determine a moisture content of soil in proximity to each of the plurality of sensors;
    inserting the probe into soil in which the moisture content is to be measured;
    positioning a wireless transmitter in communication with the plurality of sensors, the wireless transmitter operable to receive a GPS timing signal and to propagate a precise timing signal to each of the plurality of sensors.

11. The method of claim 10, wherein at least one of the plurality of sensors comprises flex circuitry attached to micro circuit boards housing logic and control circuitry.

12. The method of claim 11, wherein the flex circuitry comprises adjacent tabs, and wherein the adjacent tabs form the plates of a capacitive element of the logic and control circuitry.

13. The system of claim 10, further comprising a coating covering substantially the entirety of the probe and encasing the plurality of sensors.

14. The method of claim 10, wherein the probe comprises a cap attached to an upper end, the cap comprising internal threading allowing attachment of a slide hammer for installation and removal of the probe.

15. The method of claim 10, further comprising a battery pack in electrical communication with the wireless transmitter and/or the plurality of sensors.

16. The method of claim 15, wherein the battery pack and wireless transmitter are magnetically coupled.

17. The method of claim 10, wherein each of the plurality of sensors comprises oscillator circuitry and logic and control circuitry, and wherein the logic and control circuitry comprises a microprocessor programmed to:
 count pulses generated by the oscillator circuitry over a predetermined period of time and determine the frequency of the oscillator therefrom;
 calculate a volumetric moisture content based on the determined frequency; and
 transmit the calculated volumetric moisture content to the wireless transmitter unit for access by a remote device.

18. The method of claim 17, wherein the oscillator operates at a nominal frequency of approximately 200 MHz or greater.

* * * * *